United States Patent [19]
Cash

[11] Patent Number: 5,616,026
[45] Date of Patent: Apr. 1, 1997

[54] ORTHONDONTIC APPLIANCE AND METHOD OF MAKING THE SAME

[75] Inventor: David A. Cash, Nederland, Colo.

[73] Assignee: RMO, Inc., Denver, Colo.

[21] Appl. No.: 485,983

[22] Filed: Jun. 7, 1995

[51] Int. Cl.$^6$ ..................................................... A61C 3/00
[52] U.S. Cl. ..................................................... 433/8; 433/9
[58] Field of Search ......................... 433/8, 9, 24, 10–15; 29/160.6

[56] References Cited

U.S. PATENT DOCUMENTS

| | | | |
|---|---|---|---|
| 4,604,057 | 8/1986 | Viglietti | 433/9 |
| 4,819,316 | 4/1989 | Rossini et al. | 29/160.6 |
| 5,238,402 | 8/1993 | Röhlcke et al. | 433/2 |
| 5,267,854 | 12/1993 | Schmitt | 433/8 |
| 5,376,002 | 12/1994 | Andreiko | 433/9 |

FOREIGN PATENT DOCUMENTS 0577398  1/1994  European Pat. Off. ................... 433/8

*Primary Examiner*—Christopher A. Bennett
*Attorney, Agent, or Firm*—Sheridan Ross P.C.

[57] ABSTRACT

An at least aesthetically integral orthodontic appliance which is formed from an orthodontic base and a separately formed orthodontic body, as well as a method for making the same. In one embodiment, a base and body are separately formed by metal injection molding, the upper surface of the base having a pair of preferably mesio-distally extending alignment rails formed thereon. The lower portion of the body is positioned between these rails and forced into engagement with the base. The resulting assembly is thereafter heat treated to form an at least aesthetically appearing and preferably structurally integral orthodontic appliance by an amorphous blending of the interface between the base and body.

29 Claims, 10 Drawing Sheets

ORTHONDONTIC APPLIANCE AND METHOD OF MAKING THE SAME

FIELD OF THE INVENTION

The present invention generally relates to the field of orthodontics and, more particularly, to an at least aesthetically appearing and preferably functionally "integral" orthodontic appliance which is formed from an orthodontic body and a separate base.

BACKGROUND OF THE INVENTION

One factor which affects the commercial viability of a particular orthodontic appliance is of course the cost of the appliance. The cost of the appliance is influenced by a number of factors, one of which is the manufacturing costs. With regard to metal brackets, a wide variety of these types are manufactured in two-piece form. Specifically, the body of the bracket, which includes the tie wings, is manufactured as one part (e.g., by metal injection molding ("MIM"), while the other part, a tooth contoured bonding base, is manufactured separately (e.g., by photo etching or by stamping). The body and base are then welded or brazed together about the perimeter of the body. Although this manufacturing method produces brackets which perform suitably in many cases, the associated manufacturing costs may have a tendency to be comparatively high depending upon, for instance, the specific manufacturing sequence and the labor involved therewith. Moreover, corrosion can result from non-passive resistance welds and crevice corrosion sometimes occurs at the interface of orthodontic bodies which are welded to bases. Orthodontic bodies and bases which are joined by brazing require relatively expensive precious metal or noble alloys to avoid this type of corrosion problem.

Another method of manufacturing metal brackets is by MIM. That is, the entire bracket may be molded as a single part. U.S. Pat. No. 5,267,854 refers to such a bracket. The manufacturing costs associated with this particular method may be comparatively high due primarily to the cost of the molds. That is, depending of course upon the configuration of the particular bracket, the molds tend to be relatively complex to design and/or manufacture.

Based upon the foregoing, there continues to be a need for further improvements in the manufacture of orthodontic appliances which have commercially acceptable performance characteristics and which are commercially available at a competitive price.

SUMMARY OF THE INVENTION

One aspect of the present invention relates to a method of manufacturing at least an aesthetically, but preferably functionally as well, "integral" orthodontic appliance (i.e., of one-piece construction) from multiple parts, for instance an orthodontic base and orthodontic body. Initially, the base and body are produced as separate parts by metal injection molding, and are thus green parts. The green orthodontic base and separate green orthodontic body are thereafter placed in at least partial abutting relationship and heat treated to form the appliance. The heat treatment preferably results in the orthodontic base and body being fused together (e.g., through a fusion-sintering process involving multiple heating steps). Specifically, the base and body are preferably fused together in those locations where there was substantial contact between the base and body. This interconnection via a fusion-like bonding may be further enhanced by an amorphous blending such that the base and body become effectively an aesthetically, as well as functionally, integral structure.

The above-noted methodology may further include the step of forcing the body into engagement with the base, for instance to improve upon the establishment of the interface between the green orthodontic body and green orthodontic base. In the case where the body includes tie wings, this force may be applied to substantially only a central portion thereof so as to reduce the potential for damage to the wing tips/tie wings and/or an alteration of their relative orientations. Green parts retain somewhat of a soft/pliable/plastic-like texture such that the wing tips may be subject to deformation during the noted forcible engagement. The member which forcibly engages the body may also be contoured to substantially approximate and support the contour of the engaged portion of the body to also reduce the potential for undesired deformation of the body, regardless of the extent of the interface between the member and the green orthodontic body. Furthermore, the noted force may be applied by a spring-biased member and the amount of the force may also be limited or controlled by the spring being used. In addition, the lower surface of the base may be substantially supported during this forcible engagement. This is particularly desirable in the case where the base has a three-dimensional, arcuate or compound curve contour, such that the supporting thereof substantially retains this contour.

The above-noted methodology may also include the step of aligning the green orthodontic body onto the green orthodontic base to establish a predetermined positional relationship therebetween prior to undergoing the heat treatment, such as by incorporating the structures discussed below. The methodology may also include the step of restricting relative movement between the green orthodontic base and body in at least one of and preferably both a mesio-distal and gingival-occlusal direction.

In another aspect, the present invention is an orthodontic assembly which includes a green orthodontic body, a green orthodontic base, and structure for aligning the body onto the base to achieve a predetermined positional relationship therebetween in at least one dimension. The alignment structure may include two alignment rails on the labial surface of the orthodontic base such that a labial portion of the orthodontic body is received within the space between the rails. The alignment rails may be generally mesio-distally extending in which case the body will be disposed in a predetermined occlusal-gingival position on the body, or occlusal-gingivally extending in which case the body will be disposed in a predetermined mesio-distal position on the body. The rails not only serve the desired alignment function, but also restrict relative movement between the orthodontic base and body in at least one dimension. For instance, the rails may restrict relative mesio-distal or occlusal-gingival movements, as well as relative rotation.

The above-noted alignment structure may include a hole in at least one of the orthodontic base and body and a corresponding pin in the other such that when the pin is mounted within the hole, the body is aligned on the base with respect to at least one dimension (e.g., achieving a predetermined mesio-distal position, achieving a predetermined occlusal-gingival position). More than one "pair" of the hole/pin configuration may be utilized, and the location of such may vary. For instance, a pair of the hole/pin configuration may be mesio-distally centered, or may be off-center mesio-distally. With regard to the latter case, this may reduce assembly errors when joining angulated bracket bodies to angulated bases. If the combination of orthodontic bracket body and base is wrong, the pin and hole will not mate.

Preferably, the alignment structure utilized by the orthodontic assembly of this second aspect achieves both a predetermined mesio-distal position of the orthodontic body on the base, as well as a predetermined occlusal-gingival position. Both the alignment rails and the hole(s)/pin(s) may be utilized to provide for this function.

BRIEF DESCRIPTION OF THE DRAWINGS

FIG. 2D is a partial end view (mesio-distally) of the orthodontic body of FIG. 2A incorporating an alignment pin, shaft, projection or the like;

FIG. 3E is an end view (mesio-distally) of the base of FIG. 3A incorporating an alignment pin, shaft, projection or the like;

DETAILED DESCRIPTION

The present invention will be described in relation to the accompanying drawings which assist in illustrating various features thereof. Generally, the present invention is directed toward an "integral" orthodontic appliance which is formed from a green orthodontic body and a separate green orthodontic base. In one aspect, the green orthodontic body and green orthodontic base are assembled and processed in a manner which yields what is effectively an integrally formed orthodontic appliance. In another aspect, alignment structure is provided to assist in aligning the green orthodontic body on the orthodontic base to achieve a predetermined positional relationship therebetween. Although the present invention will be described with regard to a particular orthodontic bracket, it will be appreciated that principles of the present invention may be applicable to other types of brackets, as well as other types of orthodontic appliances which include some type of base which is interconnectable with a tooth and some type of body which is positioned on the base (e.g., molars, lingual attachments).

Figure 1:
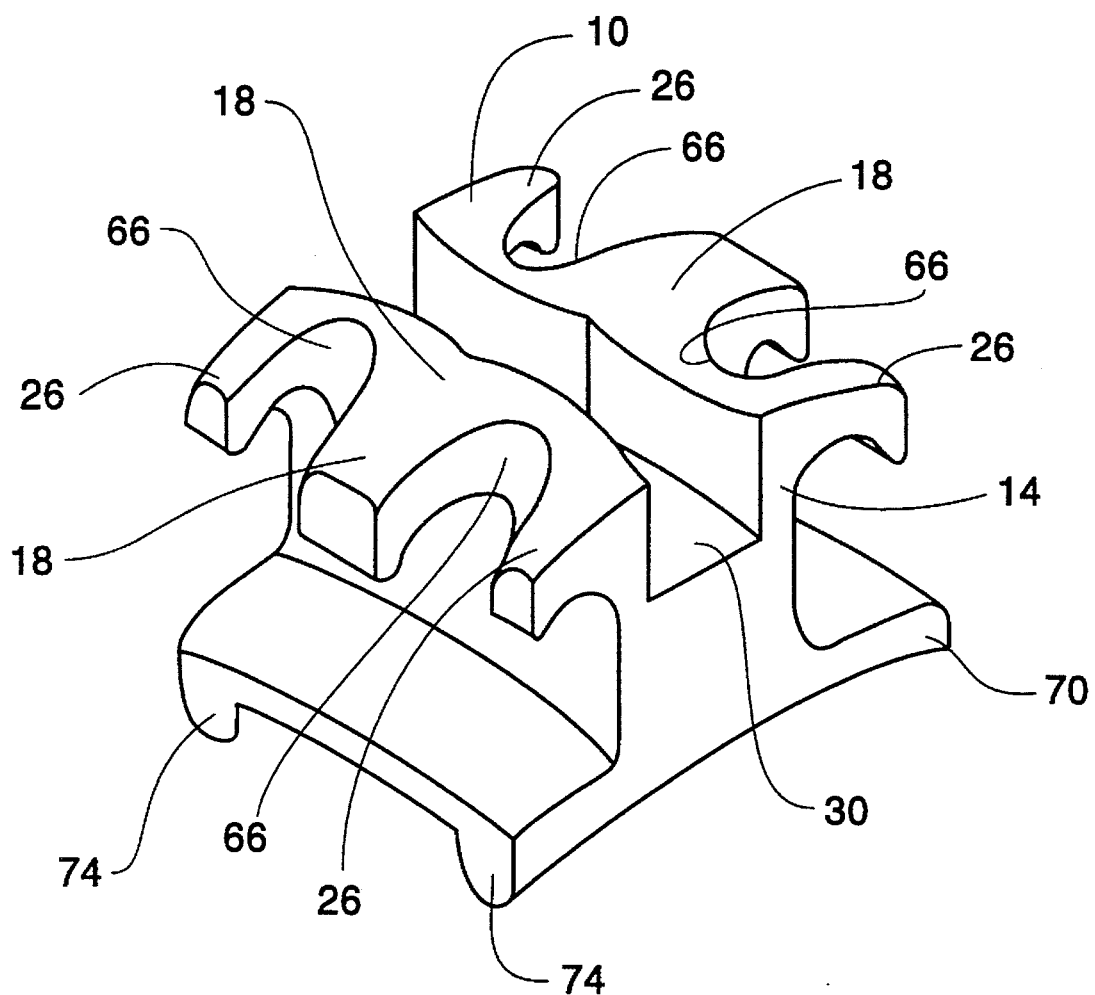
FIG. 1 is a perspective of one embodiment of an orthodontic appliance in accordance with principles of the present invention.
Figure 3D:
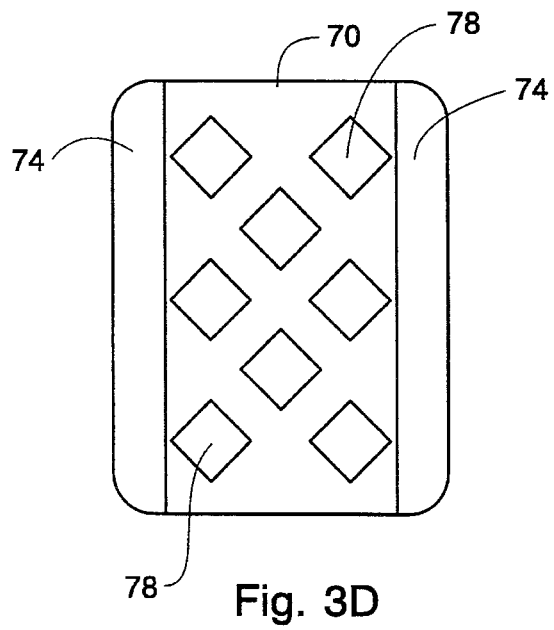
FIG. 3D is a bottom view of the base of FIG. 3A.
Figure 3A:
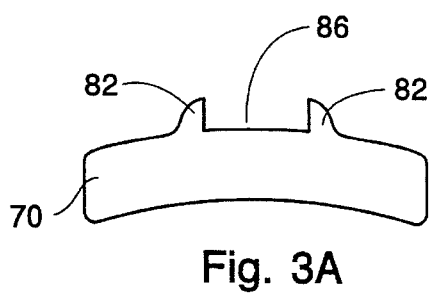
FIG. 3A is an end view (mesio-distally) of an orthodontic base which may be used in the manufacture of the orthodontic appliance of FIG. 1.

Referring to FIG. 1, the orthodontic appliance 10 generally includes an orthodontic body 14 and an orthodontic base 70 which is effectively integrally formed therewith as will be discussed below. The orthodontic body 14 has a pair of generally T-shaped, opposing tie wings 18 which define a generally mesio-distally extending arch slot 30 and includes notches 66 for facilitating ligation of an arch wire (not shown) within the slot 30 (e.g., by passing a ligature wire within the notches 66). The lower surface of the orthodontic base 70 has opposing, gingivally-occlusally extending stabilizing rails 74 with a plurality of posts 78 (FIG. 3B and 3D) positioned therebetween. The posts 78 effectively define a matrix of space for receiving bonding adhesive (not shown) to establish an interconnection of the base 70, and thus the orthodontic body 14 positioned on the upper surface of the base 70, with a tooth (not shown).

An orthodontic body 14 which may be used in the manufacture of the orthodontic appliance 10 of FIG. 1 is illustrated in FIGS. 2A–E. The body 14 is formed by metal injection molding as will be discussed in more detail below. The body 14 has the opposing T-shaped tie wings 18 with wing tips 26. These wing tips 26 extend beyond a central portion 22 of the body 14. As will be discussed below, the forces used in assembling the body 14 onto the base 70 may coincide with the central portion 22 to reduce the potential for damage to the wing tips 26 and tie wings 18.

Figure 2A:
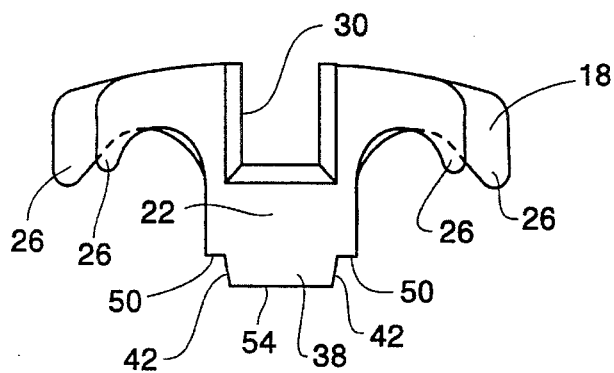
FIG. 2A is an end view (mesio-distally) of an orthodontic body which may be used in the manufacture of the orthodontic appliance of FIG. 1.
Figure 2B:
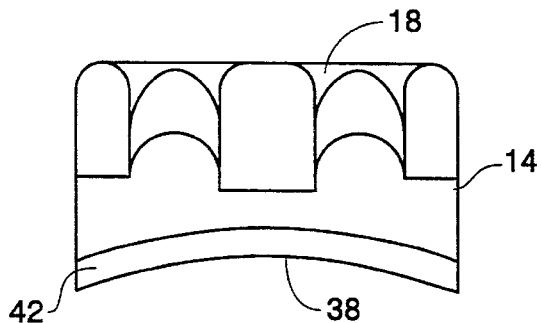
FIG. 2B is a side view (occlusally-gingivally) of the orthodontic body of FIG. 2A.
Figure 2D:
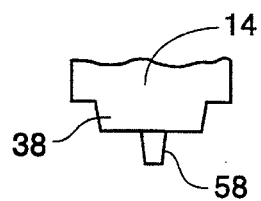
Figure 2E:
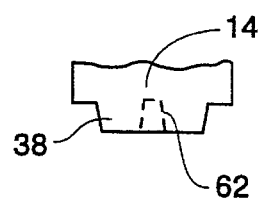
FIG. 2E is a partial end view (mesio-distally) of the orthodontic body of FIG. 2A incorporating an alignment hole.
Figure 2C:
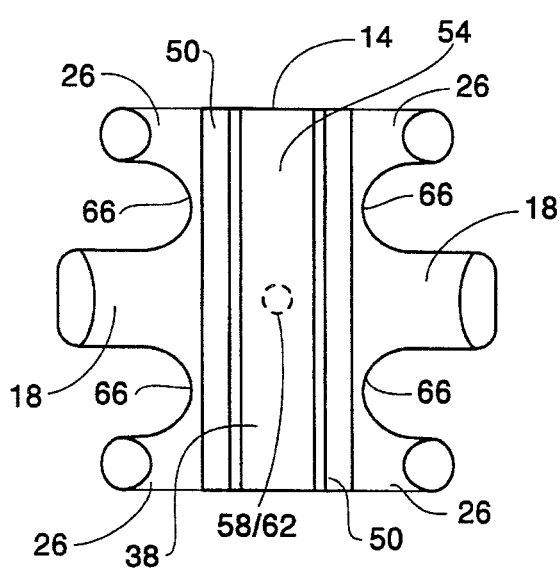
FIG. 2C is a bottom view of the orthodontic body of FIG. 2A.
Figure 2F:
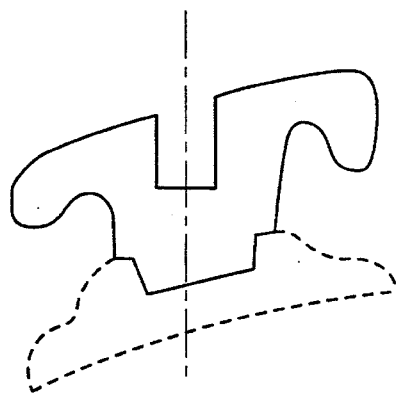
FIG. 2F is an alternate configuration for the lingual portion of the orthodontic body.
Figure 3E:
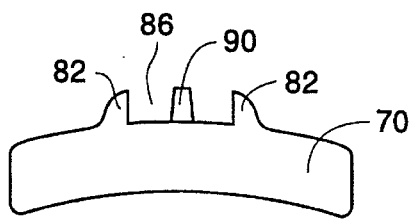
Figure 3C:
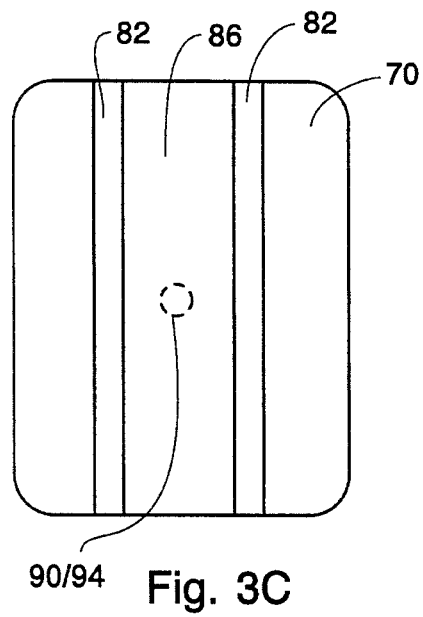
FIG. 3C is a top view of the base of FIG. 3A.
Figure 3F:
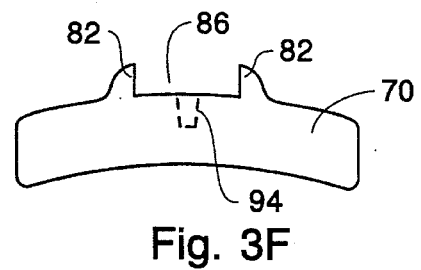
FIG. 3F is an end view (mesio-distally) of the base of FIG. 3A incorporating an alignment hole.
Figure 3B:
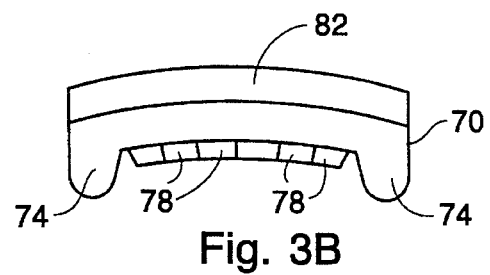
FIG. 3B side view (occlusally-gingivally) of the base of FIG. 3A.

The orthodontic body 14 also includes a mounting projection 38 which extends lingually from two gingivally/occlusally spaced lands 50 which matingly engage with the base 70 when assembled. The lands 50 may not be required in all cases, need not be planar but may assume other configurations such as arcuate, and may assume dispositions other than as shown. The mounting projection 38 is defined by two sidewalls 42 (e.g., substantially planar surfaces), at least one of which extends labially toward a reference plane which bisects (occlusally-gingivally) the slot 30 (e.g., such that the lower portion of the mounting projection 38 is narrower than the upper portion thereof) (e.g., see FIG. 2A for where both sidewalls 42 extend in the noted manner and FIG. 2F for an alternate embodiment in which only one of the sidewalls 42 extends in the noted manner). The mounting projection 38 also includes a lingual or bottom surface 54 which is preferably contoured to match that of the upper surface of the base 70 (FIGS. 3A–F) (e.g., it may have both an occlusal-gingival curvature and a mesio-distal curvature for establishing a desired interface with the orthodontic base 70, or more specifically a three-dimensional or compound curvature). As will be discussed in more detail below, the orthodontic body 14 may further include a body alignment pin 58 for interfacing with a base alignment hole 94 on the orthodontic base 70 (FIG. 3F) and/or a body alignment hole 62 which interfaces with a base alignment pin 90 on the base 70 (FIG. 3E). The body alignment hole 62 or pin 58 may be appropriately positioned on the lingual or bottom surface 54, such as at the location illustrated by dashed lines in FIG. 2C. Moreover, the body alignment hole 62 or pin serves to assist in aligning the body 14 on the base 70 mesio-distally, and also restricts relative mesio-distal movement between the body 14 and base 17 when assembled.

An orthodontic base 70 which may be used in the manufacture of the appliance 10 of FIG. 1 is illustrated in FIGS. 3A–F. The base 70 is formed by metal injection molding as will be discussed in more detail below. Initially, the base 70 includes opposing alignment rails 82 which may be integrally formed on and extend beyond the labial or upper surface of the base 70, and which nonetheless define a receiving cavity 86 for the mounting projection 38 of the orthodontic body 14. The alignment rails 82 are generally mesio-distally extending in the illustrated embodiment and limit/restrict relative occlusal-gingival movement between the body 14 and base 70 when assembled. The rails 82 also of course align the body 14 on the base 70 occlusally-gingivally. However, the alignment rails 82 could also extend occlusally-gingivally and thereby restrict relative mesio-distal movement between the body 14 and base 70 and provide for mesio-distal alignment. Regardless of orientation, the rails 82 also restrict relative rotation between the orthodontic body 14 and orthodontic base 70 when assembled in the manner discussed below.

In order to further improve upon the alignment of the green orthodontic body 14 on the green orthodontic base 70 and to further restrict relative movement therebetween, the base 70 may include a base alignment pin 90 for interfacing with an body alignment hole 62 on the lingual or bottom surface 54 of the mounting projection 38 of the body 14. Moreover, the base 70 may include a base alignment hole 94 for receiving a body alignment pin 58 which extends from the lingual or bottom surface 54 of the mounting projection 38 of the body 14. The base alignment pin 90 or hole 94 may assume an appropriate position on the labial or upper surface of the base 70, such as where depicted by dashed lines in FIG. 3C. When both the alignment rails 82 (regardless of whether mesio-distally or gingivally-occlusally extending) and an alignment pin is on at least one of the body 70 and base 14 and a corresponding alignment hole is on at least the other of the body 70 and base 14, respectively, all relative movement between the body 70 and base 14 except labially may be effectively alleviated (e.g., the alignment rails 82 may restrict relative occlusal/gingival movement and relative rotation, and the engagement of the pin in the hole restricts relative mesial/distal movement, or vice versa). Consequently, the desired orientation of the body 14 on the base 70 may be accurately achieved and maintained without the need for a fixture.

The pin 58-hole 94 alignment system, as well as the hole 62-pin 90 alignment system are illustrated as being mesio-distally centered. However, a pin/hole alignment system may be located mesio-distally off-center. This could be utilized to reduce assembly errors (when assembling the green orthodontic body 14 and orthodontic base 70), particularly in the case where the green orthodontic body 14 is an angulated bracket body and where the orthodontic base 70 is an angulated base. If the combination of a given angulated bracket body and angulated base is wrong (i.e., where an operator is attempting to install a body on the "wrong" base), the pin and hole alignment system would not match and thereby provide an indication of the "error" (i.e., the pin/hole alignment system may be further used to indicate that there is an improper combination of an angulated bracket body and angulated base). Although only one pair of the pin/hole alignment configuration is illustrated, it may be desirable to utilize more than one such pair.

Although the above-described features have been described for aligning the green orthodontic 14 on the green orthodontic base 70, other indexing systems may be utilized to assemble the green orthodontic body 14 and green orthodontic base 70. For instance, a generally circular alignment rail and a corresponding generally circular and interfacing projection could be utilized (not shown) (e.g., with the projection being positioned within the circular alignment rail). This type of indexing system would allow for selective adjustment of the green orthodontic body 14 relative to the green orthodontic base 70. Moreover, this circular rail/ projection concept would restrict both relative mesio-distal and occlusal-gingival movements. However, it would allow for relative rotation.

Another indexing system which could be used to assemble the green orthodontic body 14 and the green orthodontic base 70 would be to have at least one convex projection on one of these parts and a corresponding cavity on the other of the parts. This would allow for relative positioning of the green orthodontic body 14 on the green orthodontic base 70 in terms of angulation, torque and, mesial or distal rotation.

Figure 4A:
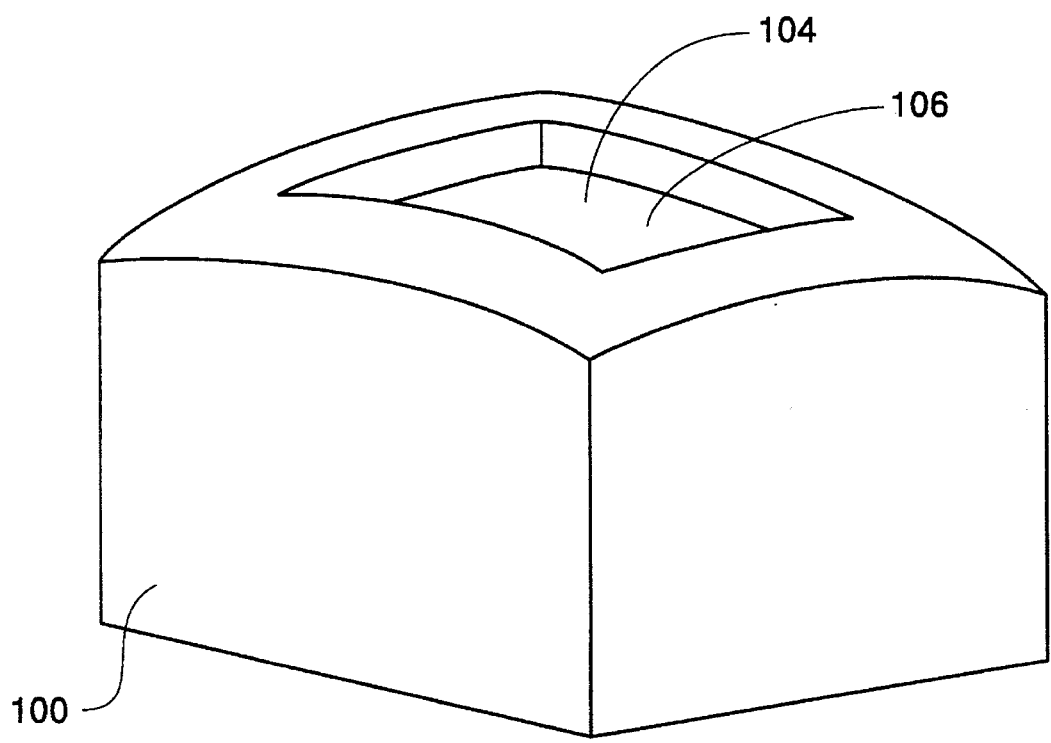
FIGS. 4A–H are views of one method for assembling the orthodontic appliance of FIG. 1 from the body of FIGS. 2A–E and the base of FIGS. 3A–F.
Figure 4C:
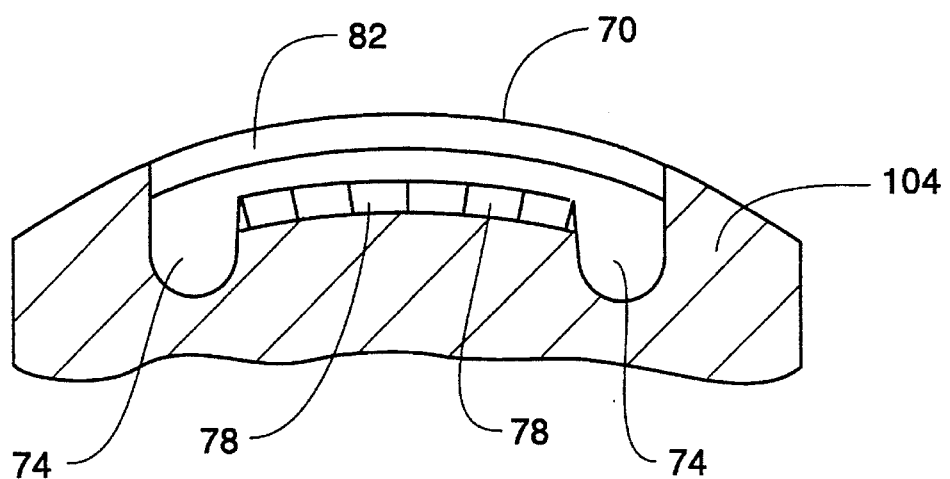
Figure 4B:
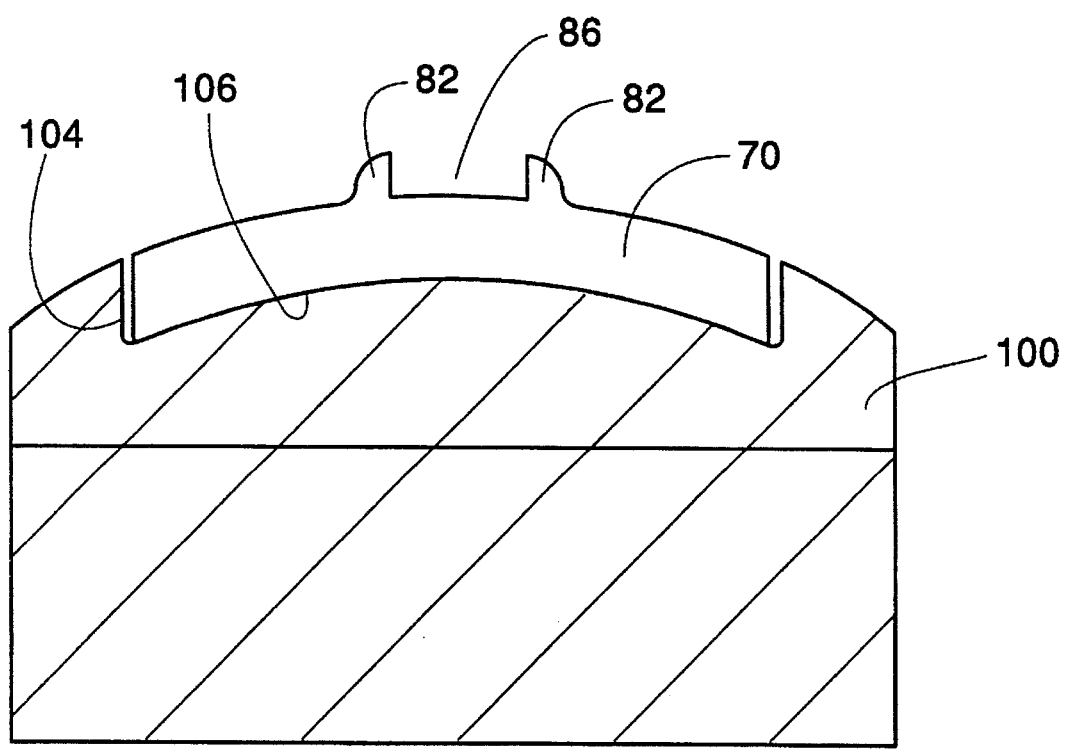

One method for assembling the body 14 of FIGS. 2A–E and the base 70 of FIGS. 3A–F is illustrated in FIGS. 4A–H. As noted, the body 14 and base 70 are separately formed via metal injection molding and are in the "green state" prior to assembly. Referring initially to FIGS. 4A–C, a jig 100 having a recess 104 formed therein may be used for retaining the orthodontic base 70 in a predetermined position and/or for supporting the base 70 during the assembly procedure. Specifically, it is desirable for the recess 104 to be dimensioned substantially similarly to the base 70 such that the jig 100 maintains the position of the base 70 therein. Moreover, preferably the floor 106 of the recess 104 substantially approximates the general contour of the lower surface of the base 70. In this regard, since the lower surface of the base 70 typically has a three-dimensional or compound curvature on its lower surface for establishing a desired interface with a tooth (not shown) when mounted thereon, the floor 106 which defines the recess 104 on the jig 100 also preferably includes the same three-dimensional contour or compound curvature. Consequently, when the body 14 and base 70 are forcibly engaged as will be discussed below, these forces are distributed and supported over substantially the entire lower surface of the base 70 (e.g., it is desirable to maximize the area over which the base 70 is supported). In the event that the stabilizing rails 74 on the bottom surface of the base 70 extend further downwardly than the posts 78, the floor 106 of the recess 104 may be configured such that it supports both the stabilizing rails 74 and the ends of the posts 78 as illustrated in FIG. 4C.

Figure 4D:
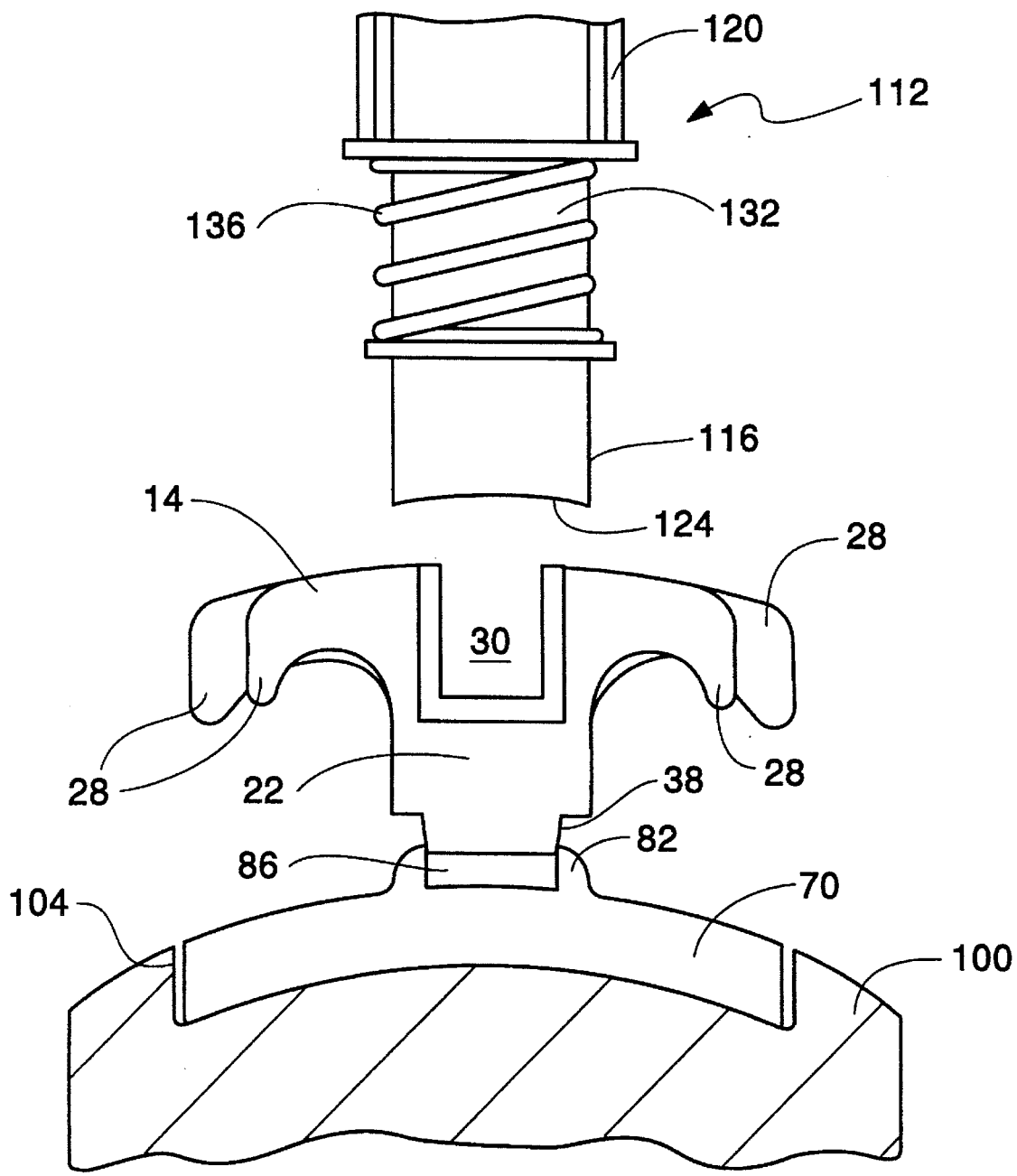

The base 70 is positioned within the recess 104 of the jig 100 and the mounting projection 38 of the orthodontic body 14 is positioned between the alignment rails 82 on the upper surface of the orthodontic base 70 as illustrated in FIG. 4D. As noted, the alignment rails 82 limit or restrict relative gingival-occlusal movement between the body 14 and base 70 in the illustrated embodiment and also serve to align the body 14 on the base 70 gingivally-occlusally. In order to further to assist in mesio-distal alignment of the body 14 on the base 70 and/or to restrict relative mesio-distal movement between the body 14 and the base 70, at least one alignment pin and alignment hole may be used as well (e.g., at least one body alignment pin 58 may extend from the lingual or bottom surface 54 of the mounting projection 38 of the body 14 for interfacing relationship with a base alignment hole 94 on the labial upper surface of the base 70). Nonetheless, the body 14 may be pressed downwardly by hand onto the base 70 with relatively small forces such that the body 14 is seated within the base receiving cavity 86 to a degree. When the base 70 and body 14 are formed by MIM, the texture of the base 70 and body 14 is still somewhat soft such that the application of these small compressive forces provide for a conforming and "tacky" engagement between the orthodontic base 70 and orthodontic body 14 to substantially maintain their relative positionings. Moreover, these relatively small forces and their location of application (preferably centrally on the body 14) do not significantly affect the configuration of the body 14 and/or base 70.

Once the body 14 is appropriately positioned on the base 70, the body 14 and base 70 may be compressed together to fully seat the mounting projection 38 of the body 14 into the receiving cavity 86 of the base 70. One way in which this may be provided is by use of a compression assembly 112, illustrated in FIG. 4D prior to engagement with the body 14 and in FIG. 4E while compressing the body 14 downwardly onto the base 70. The compression assembly 112 generally includes a drive member 120 which may be activated by, for instance, a lever interconnected therewith (not shown) to impart vertical movement to the compression assembly 112. The assembly 112 also includes a tip 116 which is preferably movable relative to the drive member 120. The tip 116 has an engaging surface 124 which preferably generally approximates the contour of the engaged portion of the orthodontic body 14. Moreover, the tip 116 may be dimensioned such that it exerts a substantial portion of the compressive forces in substantial alignment with the central portion 22 of the orthodontic body 14 as shown and which may be desirable in some instances (i.e., the force is not applied to the wing tips 26 of the tie wings 18, but is instead exerted over a centralized area of the body 14). Consequently, the potential for damage to the tie wings 18 and/or a change of orientation thereof, more particularly the wing tips 26, may be reduced. Generally, it is desirable that the forcible engagement be provided without substantially affecting the positioning of the wing tips 26, and/or otherwise deforming the assembly. Consequently, in some circumstances, it may be desirable to maximize the area of the interface between the tip 116 and the upper surface of the orthodontic body 14.

Figure 4E:
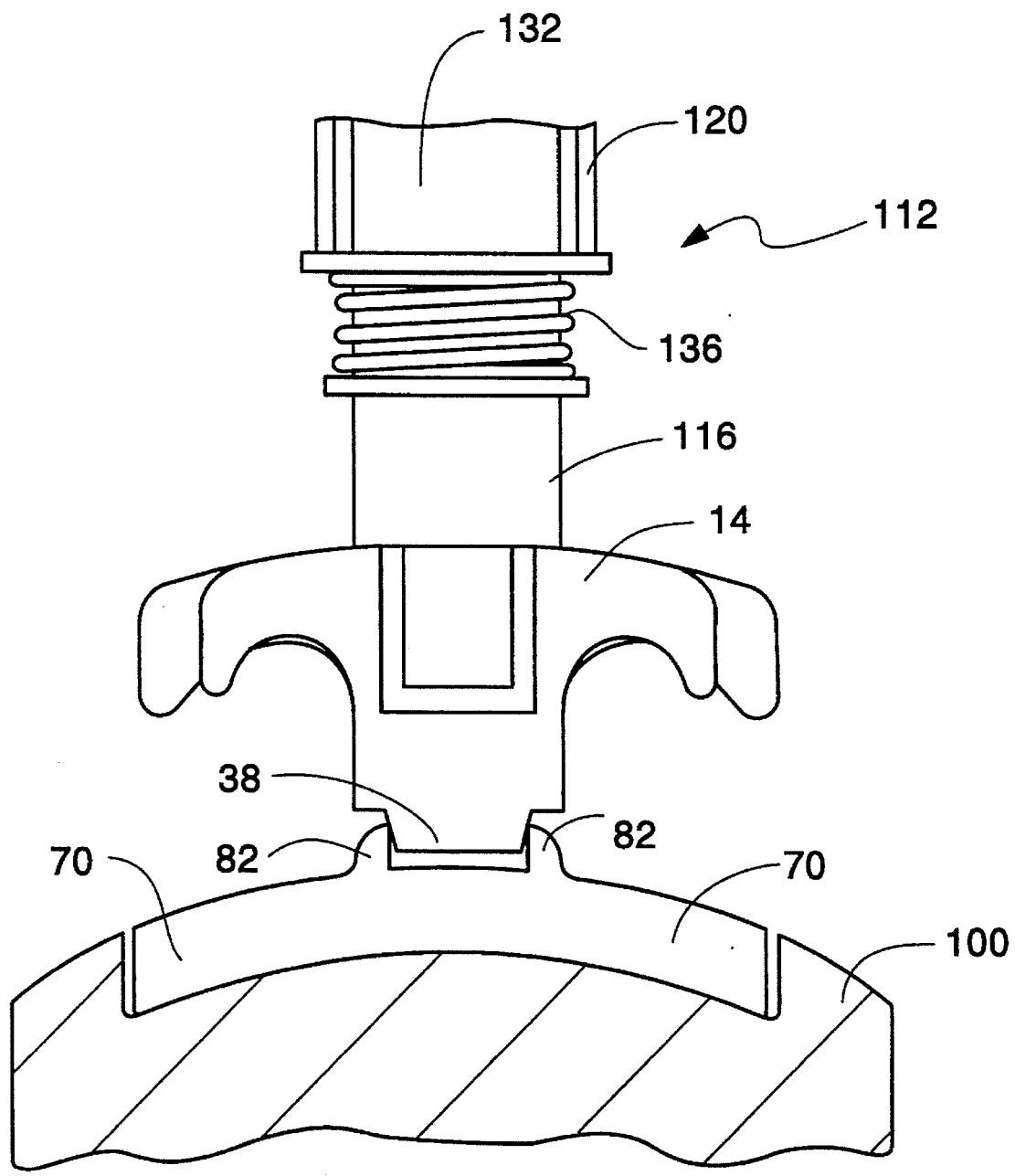

As noted, the tip 116 is preferably movable relative to the drive member 120. In this regard, the tip 116 is mounted on a tip shaft 132 which is in turn slidably engaged with the drive member 120. Moreover, a spring 136 biases the tip shaft 132, and thus the tip 116, away from the end of the drive member 120. Consequently, when the compression assembly 112, more particularly the drive member 120, is driven in a downward direction (e.g., by movement of a lever (not shown) interconnected therewith), the tip 116 engages the upper surface of the orthodontic body 14 and forces its mounting projection 38 downwardly within the receiving cavity 86 of the base 70 as illustrated in FIG. 4E. During this movement, the spring 136 may and typically does compress to a degree during this forcible engagement such that the tip shaft 132 does not move downwardly to the same extent as the drive member 120. The amount of spring force in the spring 136 may be selected such that it provides some control over this forcible engagement of the body 14 and base 70 in the noted manner.

Figure 4F:
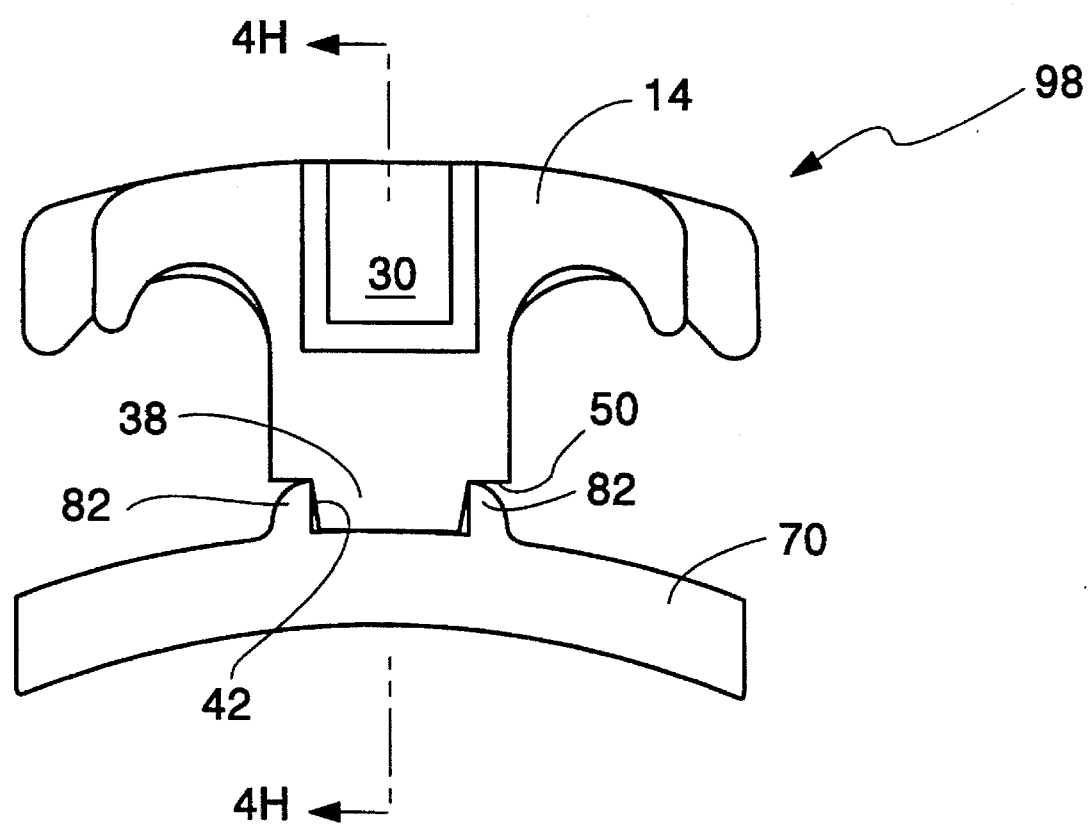
Figure 4G:
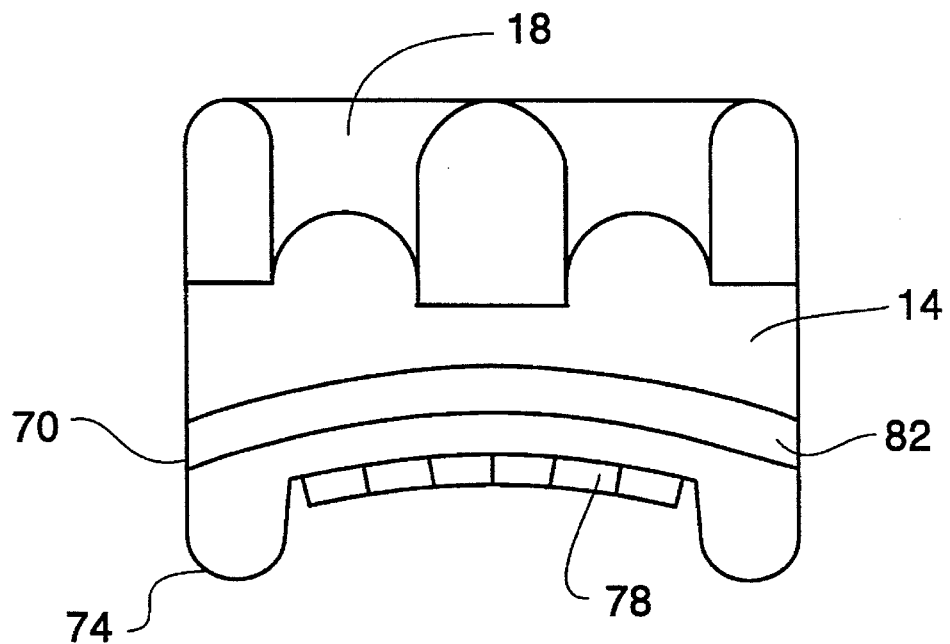
Figure 4H:
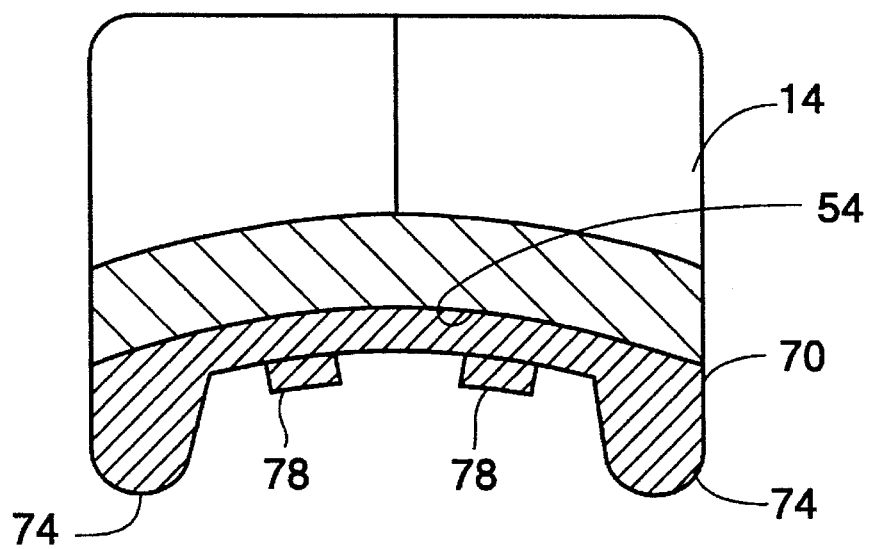

After the body 14 is fully seated within the receiving cavity 86 of the base 70 to form an assembly 98 as illustrated in FIGS. 4F–H, substantially the entire lingual or bottom surface 54 of the mounting projection 38 of the body 14 interfaces with the corresponding portion of the labial or upper surface of the base 70. This defines a surface over which the body 14 and base 70 may be interconnected by heat treatment as will be discussed in more detail below. In this case, generally the body 14 and base 70 are fused together over substantially this entire interface to define what is effectively an integrally formed orthodontic appliance 10 (FIG. 1) (e.g., fusion bonded, fusion merged). Although FIG. 4F illustrates a slight gap between the sidewalls 42 and the interior portions of the alignment rails 82, this gap may be relatively small such that there is also an interface between the alignment rails 82 and the sidewalls 42 which are fused together in the noted manner. Moreover, there is a further interface between the upper portions of the alignment rails 82 and the lands 50.

Although the above-described methodology may be utilized with a variety of dimensions for the body 14 and base 70, the configuration/dimensions of the mounting projection 38 and receiving cavity 86 may be selected to provide for an interface which provides for a desired degree of "integralness" for the appliance 10. In this regard, in one embodiment: 1) the labial/lingual extent or height of the mounting projection 38 is about 0.014 inches; 2) the dimensions of the lingual or bottom surface 54 of the mounting projection 38 are about 0.050 inches to about 0.160 inches along the mesio-distal direction and about 0.050 inches along the occlusal-gingival direction; 4) the occlusal-gingival extent of each of the lands 50 is about 0.003 inches, whereas the mesial-distal extent of such lands 50 is preferably the same as that associated with the lingual or bottom surface 54; 5) the labial/lingual extent or height of the alignment rails 82 is about 0.015 inches; and 6) the mesio-distal extent of the receiving cavity 86 is about the same as that associated with the lingual or bottom surface 54, and the gingival-occlusal extent of the receiving cavity 86 is about the same as that of the lingual or bottom surface 54.

Figure 5:
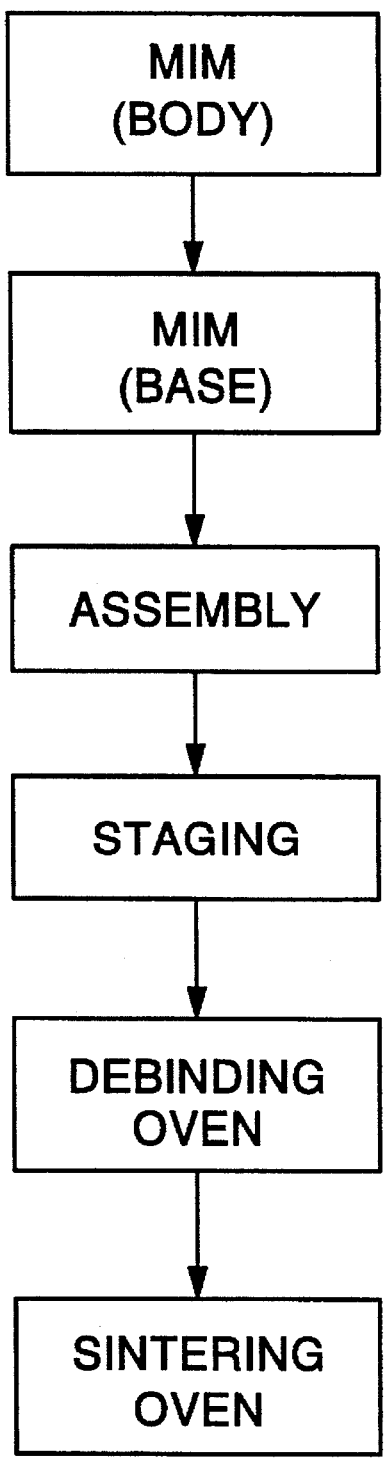
FIG. 5 is a flow chart of one embodiment of a method for the manufacturing the orthodontic appliance of FIG. 1.

The general method by which the orthodontic appliance 10 of FIG. 1 may be formed is schematically illustrated in FIG. 5. Initially, the orthodontic body 14 and the orthodontic base 70 are separately formed by metal injection molding ("MIM"). Suitable metal injection molding feedstock for forming the orthodontic body 14 and orthodontic base 70 is described in U.S. Pat. No. 4,708,741, the entire disclosure of which is incorporated by reference in its entirety herein. After the orthodontic body 14 and orthodontic base 70 are formed by MIM and thus in the green state they are assembled in the manner discussed above in relation to FIGS. 4A–H to form an assembly 98. A plurality of assemblies 98 may then be positioned in an appropriate tray (e.g., staged), transferred to an oven, and subjected to an appropriate heating treatment to, inter alia, fuse the body 14 to the base 70 preferably along the entire interface therebetween to form the orthodontic appliance 10.

The above-noted manner of heat treatment of the assemblies 98 may vary depending upon the manner in which the orthodontic body 14 and base 70 are formed and/or the materials which form the body 14 and base 70. In a presently preferred embodiment, the body 14 and base 70 are each formed by MIM and in the untreated form include about 62% metal and 38% binder, the metal powder being alloys which are suitable for use in dental applications (e.g., stainless steels such as 316 L duplex material). One type of appropriate heat treatment will be described with regard to this particular application.

Generally, the heat treatment may be classified as a vacuum sintering process which utilizes a batch furnace lined with pure carbon to provide a graphite hot zone and an outer pressure vessel which is capable of withstanding deep vacuum. One appropriate heat treatment sequence which may be employed with the body 14 and base 70 assembled in the noted matter and positioned within the furnace is generally as follows: 1) increase the temperature of the furnace from ambient to about 100° C. at a rate of 2.5° C. per minute at 5 m Torr vacuum and hold at 100° C. for a period of one hour; 2) increase the temperature of the furnace from 100° C. to 200° C. at a rate of 1.5° C. per minute at a 5 m Torr vacuum and hold at 200° C. for a period of one hour; 3) increase the temperature of the furnace from 200° C. to 300° C. at a rate of 1.5° C. per minute at a 5 m Torr vacuum and hold at 300° C. for a period of one hour; 4) increase the temperature of the furnace from 300° C. to 400° C. at a rate of 1.5° C. per minute at a 5 m Torr vacuum and hold at 400° C. for a period of one hour; 5) increase the temperature of the furnace from 400° C. to 500° C. at a rate of 1.5° C. per minute at a 5 m Torr vacuum and hold at 500° C. for a period of one hour; 6) increase the temperature of the furnace from 500° C. to 600° C. at a rate of 1.5° C. per minute at a 5 m Torr vacuum and hold at 600° C. for a period of one hour; and 7) increase the temperature of the furnace from 600° C. to 1300° C. at a rate of 1.5° C. per minute at a 1,000 m Torr vacuum and hold at 1300° C. for a period of one hour. After this treatment the temperature of the furnace thermal free falls back to room temperature and the assemblies may be removed.

Although the orthodontic appliance 10 formed in the above-described manner is referred to as being "integral" herein, there may be a density variation throughout the appliance 10, primarily at the interface between the body 14 and base 70. However, the "bond" strength between the base 14 and body 70 after undergoing the above-described heat treatment is believed to be sufficient to withstand the forces utilized in orthodontic treatment.

The foregoing description of the invention has been presented for purposes of illustration and description. Furthermore, the description is not intended to limit the invention to the form disclosed herein. Consequently, variations and modifications commensurate with the above teachings and the skill or knowledge of the relevant art, are within the scope of the present invention. The embodiments described hereinabove are further intended to explain best modes known of practicing the invention and to enable others skilled in the art to utilize the invention and such, or other embodiments and with the various modifications required by the particular applications or uses of the inventions. It is intended that the appendant claims be construed to include alternative embodiments to the extent permitted by the prior art.

What is claimed is:

1. A method for manufacturing an at least aesthetically integral orthodontic appliance, comprising the steps of:

metal injection molding a green orthodontic base;

metal injection molding a green orthodontic body;

positioning said green orthodontic base and said orthodontic body in at least partial abutting relationship; and heating said green orthodontic base and body after said positioning step; and forming said orthodontic appliance from said heating step.

2. A method, as claimed in claim 1, further comprising the step of:

aligning said green orthodontic body on said green orthodontic base to establish a predetermined positional relationship between said green orthodontic body and said green orthodontic base prior to said heating step.

3. A method, as claimed in claim 2, wherein:

said aligning step comprises using at least one pair of interfacing structures between said green orthodontic body and base.

4. A method, as claimed in claim 3, wherein:

said at least one pair of interfacing structures comprises a hole on one of said green orthodontic body and base and a pin on the other of said green orthodontic body and base.

5. A method, as claimed in claim 4, wherein:

said hole and pin are mesio-distally centered.

6. A method, as claimed in claim 4, wherein:

said hole and pin are off-center mesiodistally.

7. A method, as claimed in claim 2, wherein:

said aligning step comprises using at least two pair of interfacing structures between said green orthodontic body and base.

8. A method, as claimed in claim 1, further comprising the step of:

restricting relative movement between said green orthodontic base and body in at least one of a mesio-distal and gingival-occlusal direction after said positioning step.

9. A method, as claimed in claim 1, wherein:

said metal injection molding a green orthodontic base step comprises forming a pair of alignment rails on an upper surface of said green orthodontic base; and wherein said positioning step comprises positioning a lower portion of said green orthodontic body between said pair of alignment rails.

10. A method, as claimed in claim 9, wherein:

said positioning step further comprises wedging said lower portion of said green orthodontic body between said pair of alignment rails.

11. A method, as claimed in claim 10, wherein:

said alignment rails are mesio-distally extending.

12. A method, as claimed in claim 1, further comprising the steps of:

forming one of a hole and a projection in an upper surface of said green orthodontic base;

forming the other of said hole and said projection on a lower surface of said green orthodontic body, said positioning step comprising positioning said projection within said hole.

13. A method, as claimed in claim 1, further comprising the step of:

forcing said orthodontic body into engagement with said orthodontic base.

14. A method, as claimed in claim 13, wherein:

said orthodontic body comprises at least one pair of tie wings which define a mesio-distally extending archwire slot, each said tie wing having at least one tie wing tip which extends away from said archwire slot and is displaced from a central portion of said bracket body; and said forcing step comprises engaging substantially only said central portion of said bracket body.

15. A method, as claimed in claim 14, wherein:

said forcing step further comprises the step of substantially matingly engaging said central portion and substantially retaining an orientation of said tie wing tips relative to said orthodontic base during said forcing step.

16. A method, as claimed in claim 13, wherein:

said forcing step comprises engaging said orthodontic body with a spring-biased member.

17. A method, as claimed in claim 13, wherein:

said forcing step comprises matingly engaging a forcing member with at least a portion of an upper surface of said orthodontic body.

18. A method, as claimed in claim 13, wherein:

said producing an orthodontic base step comprises forming both a predetermined mesio-distal and occlusal-gingival curvature on a bottom surface of said orthodontic base opposite a top surface on which said orthodontic body is mounted, and said method further comprises the step of supporting said bottom surface of said green orthodontic base during said forcing step to substantially retain said predetermined mesio-distal and occlusal-gingival curvatures.

19. A method, as claimed in claim 1, wherein:

said heating step comprises sintering said orthodontic base and body.

20. A method, as claimed in claim 1, further comprising the steps of:

centering said green orthodontic body mesio-distally on said green orthodontic base; and centering said green orthodontic body gingivally-occlusally on said green orthodontic base.

21. A method, as claimed in claim 1, further comprising the steps of:

restricting relative mesial-distal movement between said green orthodontic body and said green orthodontic base before said heating step; and restricting relative occlusal-gingival movement between said green orthodontic body and said green orthodontic base before said heating step.

22. A method, as claimed in claim 1, wherein said metal injection molding steps each comprise metal injection molding said green orthodontic base and body from a metal powder and binder, and wherein said heating step comprises the steps of:

heating said green orthodontic base and body to remove a substantial portion of said binder from each of said green orthodontic base and body;

heating said green orthodontic base and body to remove a substantial portion of oxides on exposed surfaces of each of said green orthodontic base and body;

heating said green orthodontic base and body to create an alloy from said metal powder, densify said orthodontic base and body, and realize an amorphous blending of said orthodontic base and body to fuse said orthodontic body and base together.

23. An orthodontic assembly, comprising:

a metal injection molded orthodontic body;

a metal injection molded orthodontic base separate from said body; and means for aligning said orthodontic body on said orthodontic base to achieve a predetermined positional relationship between said orthodontic body and said orthodontic base.

24. An orthodontic assembly, as claimed in claim 23, wherein:

said orthodontic base comprises labial and lingual surfaces and first and second rails projecting labially from said labial surface of said orthodontic base, said first and second rails comprising said means for aligning; and said orthodontic body comprises first and second portions, said first portion being positioned between said first and second rails and said second portion extending labially beyond said first and second rails.

25. An orthodontic assembly, as claimed in claim 24, wherein:

said first and second rails are mesio-distally extending.

26. An orthodontic assembly, as claimed in claim 24, wherein:

said means for aligning further comprises at least one hole in at least one of said orthodontic base and said orthodontic body and a corresponding a pin member for each said hole on the other of said orthodontic body and said orthodontic base, said at least one hole and said corresponding pin member being disposed between said first and second rails.

27. An orthodontic assembly, as claimed in claim 24, wherein:

said first and second rails extend in one of a mesio-distal direction and occlusal-gingival direction, and wherein said orthodontic assembly further comprises means for restricting movement between said orthodontic base and body in the other of said mesio-distal direction and said occlusal-gingival direction.

28. An orthodontic assembly, as claimed in claim 23, wherein:

said means for aligning comprises at least one hole in at least one of said orthodontic base and said orthodontic body and a corresponding pin member for each said hole on the other of said orthodontic body and said orthodontic base.

29. An orthodontic assembly, as claimed in claim 27, wherein:

said corresponding pin member is tapered.

* * * * *